(12) United States Patent
Serrero et al.

(10) Patent No.: US 8,088,373 B2
(45) Date of Patent: *Jan. 3, 2012

(54) AUTOCRINE GROWTH FACTOR RECEPTOR ANTIBODIES AND METHODS

(75) Inventors: Ginette Serrero, Ellicott City, MD (US); Le Sun, Beijing (CN)

(73) Assignee: A&G Pharmaceutical, Inc., Columbia, MD (US)

( * ) Notice: Subject to any disclaimer, the term of this patent is extended or adjusted under 35 U.S.C. 154(b) by 114 days.

This patent is subject to a terminal disclaimer.

(21) Appl. No.: 12/142,465

(22) Filed: Jun. 19, 2008

(65) Prior Publication Data

US 2008/0311120 A1 Dec. 18, 2008

Related U.S. Application Data

(63) Continuation of application No. 10/298,540, filed on Nov. 19, 2002, now Pat. No. 7,411,045.

(60) Provisional application No. 60/427,220, filed on Nov. 19, 2002.

(51) Int. Cl.
*A61K 39/395* (2006.01)

(52) U.S. Cl. .................................. 424/130.1; 424/141.1

(58) Field of Classification Search ........................ None
See application file for complete search history.

(56) References Cited

U.S. PATENT DOCUMENTS

| | | | |
|---|---|---|---|
| 5,416,192 A | 5/1995 | Shoyab et al. |
| 5,709,858 A | 1/1998 | Godowski et al. |
| 5,725,856 A | 3/1998 | Hudziak et al. |
| 6,309,826 B1 | 10/2001 | Serrero |
| 6,511,986 B2 | 1/2003 | Zhang et al. |
| 6,558,668 B2 | 5/2003 | Liau |
| 6,570,002 B1 | 5/2003 | Hardwick et al. |
| 6,586,395 B1 | 7/2003 | Kiefer et al. |
| 6,670,183 B2 | 12/2003 | Serrero |
| 6,720,159 B1 | 4/2004 | Serrero |
| 6,824,775 B2 | 11/2004 | Serrero |
| 6,881,548 B2 | 4/2005 | Serrero |
| 7,091,047 B2 | 8/2006 | Serrero |
| 7,368,428 B2 | 5/2008 | Serrero |
| 7,411,045 B2 | 8/2008 | Serrero et al. |
| 2002/0094966 A1 | 7/2002 | Serrero |
| 2003/0092661 A1 | 5/2003 | Serrero |
| 2003/0215445 A1 | 11/2003 | Serrero |
| 2004/0131618 A1 | 7/2004 | Serrero |
| 2005/0106150 A1 | 5/2005 | Serrero |
| 2005/0175616 A1 | 8/2005 | Kiener et al. |
| 2007/0015225 A1 | 1/2007 | Serrero |
| 2007/0065887 A1 | 3/2007 | Kinch |
| 2008/0114070 A1 | 5/2008 | Serrero |
| 2008/0145369 A1 | 6/2008 | Serrero |
| 2008/0311120 A1 | 12/2008 | Serrero et al. |
| 2009/0010931 A1 | 1/2009 | Serrero |
| 2009/0203047 A1 | 8/2009 | Serrero |

FOREIGN PATENT DOCUMENTS

| | | |
|---|---|---|
| WO | WO-9115510 | 10/1991 |
| WO | WO-93/15195 | 8/1993 |
| WO | WO-9852607 | 11/1998 |
| WO | WO-0231198 | 4/2002 |
| WO | WO-02102229 | 12/2002 |
| WO | WO-02102306 | 12/2002 |
| WO | WO-2004039244 | 5/2004 |
| WO | WO-2004045544 | 6/2004 |
| WO | WO-2004060280 | 7/2004 |
| WO | WO-2004078782 | 9/2004 |
| WO | WO-2005000207 | 1/2005 |
| WO | WO-2005000240 | 1/2005 |
| WO | WO-2005011590 | 2/2005 |
| WO | WO-2006044566 | 4/2006 |

OTHER PUBLICATIONS

Taber's Cyclopedic Medical Dictionary (1985, F.A. Davis Company, Philadelphia, p. 274.*
Busken, C et al, Digestive Disease Week Abstracts and Itinerary Planner, 2003, abstract No: 850.*
Kaiser, Science, 2006, 313, 1370.*
Krontiris and Capizzi, Internal Medicine, 4th Edition, Editor-in-chief Jay Stein, Elsevier Science, 1994 Chapters 71-72, pp. 699-729.*
Carter, S. K. et al. Chemotherapy of Cancer; Second edition; John Wiley & Sons: New York, 1981; appendix C.*
Ben-Efraim, Tumor Biology 1999; 20: 1-24.*
Marincola et al., Trends in Immunology 2003; 24: 334-341.*
Frazer, I., Expert. Opin. Pharmacother. 2004; 5: 2427-2434.*
Runquing Lu, et al. -"Inhibition of PC cell-derived growth factor (PCDGF, epithelin/granulin precursor) expression by antisense PCDGF cDNA transfection inhibits tumorigenicity of the human breast carcinoma cell line MDA-MB-468," PNAS, vol. 97, No.. 8, Apr. 11, 2000, pp. 3993-3998. Vijay Bhandari, et al.- Isolation and sequence of the granulin precursor cDNA from human bone marrow reveals tandem cysteine-rich granulin domains, Proc. Natl. Acad. Sci. USA, vol. 89, Mar. 1992, pp. 1715-1719.
Zhiheng He, et al. Progranulin Gene Expression Regulates Epithelial Cell Growth and Promotes Tumor Growth in Vivo[1], CanCer Research 59, Jul. 1, 1999, pp. 3222-3229.
Haidi Zhang, et al.- "Inhibition of tumorigenicity of the teratoma PC cell line by transfection with antisense CDNA for PC cell-derived growth factor (PCDGF, epithelin/granulin precursor)." Proc. Natl. Acad. Sci. USA, vol. 95, Nov. 1998, pp. 14202-14207.
International Search Report dated May 13, 2003.

(Continued)

*Primary Examiner* — Missok Yu
*Assistant Examiner* — Mark Halvorson
(74) *Attorney, Agent, or Firm* — Womble Carlyle Sandridge & Rice LLP (57) ABSTRACT

Disclosed herein are antitumor compositions and methods of interfering with the biological activity of PC cell derived growth factor (PCDGF), anti-PCDGF receptor antibodies, fragments thereof, and methods of making anti-PCDGF receptor antibodies. The methods involve inhibiting the proliferation of tumor cells expressing the PCDGF receptor by contacting the surface of the cell with anti-PCDGF receptor antibodies. Anti-PCDGF receptor antibodies are capable of binding to the surface of a cell and interfering with the binding of PCDGF to its receptor. Also provided are compositions comprising anti-PCDGF receptor antibodies and cytotoxic molecules (e.g., toxins, oncotoxins, mitotoxins, immunotoxins, and antisense oligonucleotides).

16 Claims, 8 Drawing Sheets

OTHER PUBLICATIONS

Zhang Haidi, "Overexpression Of PC Cell Derived Growth Factor (PCDGF) Contributes To the Highly Tumorigenic Properties Of Producer Cell Line PC" a Dissertation submitted in partial fulfillment of the requirements for the degree of Doctor of Philosophy, Chemistry, Fallof 1997, 143 pages, Clarkson University.

Zhang Haidi, "Overexpression of PC cell derived growth factor (PCDGF) contributes to the highly tumorigenic properties of producer cell line PC," Diss, Abstr. Int., vol. 58, No. 11, 1998, p. 5814-B XP001025915, abstract.

Vijay Bandhari and Andrew Bateman, "Structure and Chromosmal Location of the human granulin gene, " Biochemical and Biophyscal Research Communication, vol. 188, No. 1, 1992, pp. 57-63, XP001018991, Abstract , Fig. 2.

Bhandari et al., "The Complementary Deoxyribonucleic Acid Sequence, Tissue Distribution, and Cellular Localization of the Rat Granulin Precursor," Endocrinology, vol. 133, No. 6, 1993, pp. 2682-2689, XP001021601.

Haidi Zhang and Ginette Serrero, "Inhibition of the tumorigenicity of the teratoma PC cell line by transfection with antisense cDNA for PC cell-derived growth factor (PCDGF, epithelin/granulin precursor), " PNAS, vol. 95, Nov. 1998, pp. 14202-14207, XP002177206.

European Search Report dated Oct. 23, 2001.

Y. Shechter, et al., "Mouse Antibodies to the Insulin Receptor Developing Spontaneously As Anti-idiotypes."The Journal of Biological chemistry, vol. 259 No. 10, pp. 6411-6415, 1984.

I. R. Cohan, et al.- "Production and Properties of Anti-idiotypic Antibodies that recognize Insulin Receptor,"Methods in Enzymology, vol. 178, pp. 300-313, 1989.

Ran Hu, et al.- "Production and characterization of monoclonal anti-idiotypic antibody exhibiting a catalytic activity similar to carboxypeptidase A," Journal of Biotechnology 61, 1998, pp. 109-115.

Y. Shechter, et al. "Autoantibodies to Insulin Receptor Spontaneously Develop as Anti-Idiotypes in Mice Immunized with Insulin,"Science, vol. 216, Apr. 1982, pp. 542-545.

B. Avalle, et al. -"Functional mimicry: elicitation of a monoclonal anti-idiotypic antibody hydrolyzing β-lactams," The FASEB Journal, vol. 12, Aug. 1998, pp. 1055-1061.

A. Kolesnikov, et al.- "Enzyme mimicry by the antidiotypic antibody approach," PNAS, vol. 97, No. 25, Dec. 2000, pp. 13526-13531.

A. D. Strosberg, "Interaction of Anti-idiotypic Antibodies with Membrane Receptors: Practical Considerations." Methods of Enzymology, vol. 178, pp. 178-265 plus Table of Contents, 1989.

S. W. Bright, et al.- "Monoclonal Antibodies As Surrogate Receptors in A High Throughput Screen For Compounds that Enhance Insuline Sensitifity," Life Sciences, vol. 61, No. 23, 1997, pp. 2305-2315.

C. Monfardini, et al.-"Recombinant Antibodies in Bioactive Peptide Design(*)," vol. 270, No. 12, Issue of Mar. 1995, The American Society for Biochemistry and Molecular Biology, pp. 6628-6638.

"The Study of Antibody Recognition." Antibody Resource Page, Feb. 1998, 10 pages.

Plowman et al., -"The Epithelin Precursor Encodes Two Proteins with Opposing Activities on Epithelial Cell Growth," Journal of Biological Chemistry, vol. 267, No. 18, Jun. 1992, pp. 13073-13078, XP001018992.

Serrero G. et al., Effects of Testosterone on the Growth Properties and on Epidermal Growth Factor Receptor Expression in the Teratoma-derived Tumorigenic Cell Line 1246-3A, Cancer Research 52, 1992, pp. 4242-4247.

Alberts et al., Molecular Biology of the Cell, Garland Publishing, Inc. 1983.

Cross M. et al., Growth Factors in Development , Transformation and Tumorigenesis, Cell, vol. 64, pp. 271-280, 1991.

Spron M. B. et al., Autocrine Secretion and Malignant Transformation of Cells, The New England Journal of Medicine, vol. 303, 1980, pp. 878-880.

Zhou J. et al., Purification of an Autocrine Growth Factor Homologous with Mouse Epithelin Precursor from a Highly Tumorigenic Cell Line, The Journal of Biological Chemistry, vol. 268, No. 15, 1993, pp. 10863-10869.

Bateman A. et al., Granulins, a Novel Class of Peptide from Leukocytes, Biochemical and Biophysical Research Communications, vol. 173, No. 3, 1990, 1161-1168.

Nestor J. et al. , A Synthetic Fragment of Rat Transforming Growth Factor with Receptor Binding and Antigenic Properties, vol. 129, No. 1, 1985, pp. 226-232.

Adelman J. et al., In Vitro Deletional Mutagenesis for Bacterial Production of the 20,000-Dalton Form of Human Pituitary Growth Hormone, DNA, vol. 2, No. 3, 1983, pp. 183-193.

Serrero G. et al., An In Vitro Model to Study Adipose Differentiation in Serum-Free Medium, Analytical Biochemistry 120, 1982, pp. 351-359.

Serroro-Dave, G., Study of a Teratoma-Derived Adipogenic Cell Line 1246 and Isolation of an Insulin-Independent Variant in Serum-Free Medium, Cancer Center, University of California, pp. 366-376.

Serrero G., Tumorigenicity Associated with Loss of Differentiation and of Response to Insulin in the Adipogenic Cell Line 1246, In Vitro Cellular & Developmental Biology, vol. 21, No. 9, 1985, pp. 537-540.

Serrero G. et al., Decreased Transforming Growth Factor-β Response and Binding in Insulin-independent Teratoma-Derived Cell Lines with Increased Tumorigenic Properties, Journal of Cellular Physiology, 149, 1991, pp. 503-511.

Arteaga C. et al., Growth Inhibition of Human Breast Cancer Cells In Vitro with an Antibody against the Type I Somatomedin Receptor, Cancer Research 49, 1989, pp. 6237-6241.

Schofield P. et al, The Biological Effects of a High Molecular Weight Forms of IGFII in a Pluripotential Human Teratocarcinoma Cell Line, Anticancer Research 14, 1994, pp. 533-538.

Trojan J. et al., Gene therapy of murine teratocarcinoma: Separate functions for insulin-Like growth factors I and II in immunogenicity and differentiation, Proc. Natl. Acad. Sci. USA, vol. 91, 1994, pp. 6088-6092.

Trojan J. et al, Treatment and Prevention of Rat Glioblastoma by Immunogenic C6 Cells Expressing Antisense Insulin-Like Growth Factor I RNA, Science, vol. 259, 1993, pp. 94-96.

Kohler G., et al. Continuous cultures of fused cells secreting antibody of predefined specificity, Nature vol. 256, 1975, pp. 495-497.

De St. Groth, et al., Production of Monoclonal Antibodies, Strategy and Tactics, Journal of Immunology Methods, 35, 1980, pp. 1-21.

Schreier M., et al., Hybridoma Techniques, Cold Spring Harbor Laboratory, 1980.

Cabilly S., et al., Generation of antibody activity from immunoglobulin polypeptide chains produced in *Escherichia coli*, Proc. Natl. Acad. Sci. USA vol. 81, 1984, pp. 3273-3277.

Morrison S. et al., Chimeric human antibody molecules: Mouse antigen-binding domains with human constant region domains, Proc. Natl. Aca. Sci. USA, vol. 81, 1984, pp. 6851-6855.

Liu A. et al., Chimeric mouse-human IgG1 antibody that can mediate lysis of cancer cells, Proc. Natl. Acad. Sci. USA, vol. 84, 1987, pp. 3439-3443.

Better M. et al., *Escherichia coli* Secretion on an Active Chimeric Antibody Fragment, Science, vol. 240, 1988, pp. 1041-1043.

Riechman I. et al., Reshaping human antibodies for therapy, Nature, vol. 332, 1988, pp. 323-327.

Baca M. et al., Antibody Humanization Using Monovalent Phage Display, J. Biol. Chem., vol. 272, No. 16, 1997, pp. 10676-10684.

Rosok M. J., A Combinatorial Library Strategy for the Rapid Humanization of Anticarcinoma BR96 Fab. Biol. Chem. vol. 271, No. 37, 1996, pp. 22611-22618.

Wahl R. L. et al., Improved Radioimaging and Tumor Localization with Monoclonal F(ab'), The Journal of Nuclear Medicine, vol. 24, No. 4, 1983, pp. 316-325.

Mulshine J. L., Clinical Use of a Monoclonal Antibody to Bombesin-lik Peptide in Patients with Lung Cancer, Annals New York Academy of Sciences, pp. 360-372, 1988.

Munroe S. H., Antisense RNA inhibits splicing of pre-mRNA in vitro, The EMBO Journal , vol. 7, No. 8, 1988, pp. 2523-2532.

Mulis K. B. et al., Specific Synthesis of DNA in Vitro via a Polymerase-Catalyzed Chain Reaction, Methods in Enzymology, vol. 155, 1987, pp. 335-350.

Mercola D. et al., Antisense approaches to cancer gene therapy, Cancer Gene Therapy, vol. 2, No. 1, 1995, pp. 47-59.

Wagner R. W. et al., Gene inhibition using antisense oligodeoxynucleotides, Nature, vol. 372, 1994, pp. 333-335.

Maniatis T. et al., Molecular Cloning: A Laboratory Manual, Cold Spring Harbor Laboratory, 1982.

Brysch W. et al., Design and Application of Antisense Oligonucleotides in Cell Culture, in Vivo, and asTherapeutic Agents, Cellular and Molecular Neurobiology, vol. 14, No. 5, 1994, pp. 557-568.

Helene C., Rational Design of Sequence-specific Oncogene Inhibitors Based on Antisense and Antigene Oligonucleotides, EUR J Cancer, vol. 27, No. 11, 1991, pp. 1466-1471.

Giles R. V. et al., Optimization of Antisense Oligodeoxynucleotide Structure for Targeting ber-abl mRNA Blood, vol. 86, No. 2, 1995, pp. 744-754.

Thaler D. S. et al., Extending the chemistry that supports genetic information transfer in vivo; Phosphorothicate DNA, phosphorothicate RNA, 2'-O-methyl RNA and methylphosphonate DNA, Proc. Natl. Acad. Sci. USA, vol. 93, 1996, pp. 1352-1356.

Gryaznov S. et al., Oligonucleotide N3'-P5' phosphoramidates as antisense agents, Nucleic Acids Research, vol. 24, No. 8, 1996, pp. 1508-1514.

Lappalainen K. et al., Cationic liposomes improve stability and intracellular delivery of antisenses oligonucleotides into CaSki cells, Biochimica et Biophysica Acta 1196, 1994, pp. 201-208.

Ensoli B. et al., Block of AIDS-Kaposi's Sarcoma (kS) cell growth, angiogenesis, and lesion formation in nude mice by antisense oligonucleotide targeting basic fibroblast growth factor, The Journal of Clinical Investigation, Inc. vol. 94, 1994, pp. 1736-1746.

Peng B. et al., Growth Inhibition of Malignant CD5+b (B+1) Cells by Antisense IL-10 Oligonucleotide, Leukemia Research, vol. 19, No. 3, 1995, pp. 159-167.

Donovan R. S. et al. Review: Optimizing inducer and culture conditions for expression of foreign proteins under the control of the lac promoter, Journal of Industrial Microbiology, 16, 1996, pp. 145-154.

Cenatiempo Y., Prokaryotic gene expression in vitro: Transcription-translation coupled systems, Biochimie, 68, 1986, pp. 505-515.

Gottesman S., Bacterial Regulation: Global Regulatory Networks, Annual Review of Genetics., 18, 1984, pp. 415-441.

Hamer D. H. et al., Regulation In Vivo of a Cloned Mammalian Gene: Cadmium Induces the Transcription of a Mouse Metallothionien Gene in SV40 Vectors, Journal of Molecular and Applied Genetics, vol. 1, No. 4, 1982, pp. 273-288.

McKnight S. L., Functional Relationships between Transcriptional Control Signals of the Thymidine Kinase Gene of Herpes Simplex Virus, Cell, vol. 31, 1982, pp. 355-365.

Johnston S. A. et al., Isolation of the yeast regulatory gene GAL4 and analysis of its dosage effects on the galactose/melibiose regulon, Proc. Natl. Acd. Sci. USA, 79, 1982, pp. 6971-6975.

Benoist C. et al., In Vivo sequence requirements of the SV40 early promoter region, Nature, vol. 290, 1981, pp. 304-310.

Anderson S. et al., Cloning, Structure, and Expression of the Mitochondrial Cytochrome P-450 Sterol 26-Hydroxylase, a Bile Acid Biosynthetic Enzyme, The Journal of Biological Chemistry, vol. 264, No. 14, 1989, pp. 8222-8229.

Sepp-Lorenzino L. et al., Insulin and Insulin-like Growth factor Signaling Are Defective in the MDA MB-468 Human Breast Cancer Cell Line, Cell Growth & Differentiation, vol. 5, 1994, pp. 1077-1083.

Culouscou J. M. et al., Biochemical Analysis of the Epithelin Receptor, The Journal of Biological chemistry, vol. 268, No. 14, 1993, pp. 10458-10462.

Siegall C. B., Targeted Toxins as Anticancer Agents, Cancer, vol. 74, No. 3, 1994, pp. 1006-1012.

J. Barnwell, et al., "A Human 88-kD Membrane Glycoprotein (CD36) Functions in Vitro as a Receptor for a Cytoadherence Ligand on Plasmodium falciparum-infected Erythrocytes," J. Clin. Invest., Sep. 1989, vol. 84, pp. 765-772.

R. Daniel, et al., "Cellular localization of Gene Expression for Progranulin," Journal of Histochemistry and Cytochemistry, Jul. 2000, vol. 48, No. 7, pp. 999-1009.

Hoque, et al., "The growth factor granulin interacts with cyclin T1 and modulates P-TEfb-dependent transcription," Mol Cell Biol., Mar. 2003, vol. 23, No. 5, pp. 1688-1702.

MB Jones et al., "The granulin-epithelin precursor/PC-cell-derived growth factor is a growth factor for epithelial ovarian cancer," Clin Cancer Res., Jan. 2003, vol. 9, No. 1, pp. 44-51.

WE Kim et al., "PC cell-derived growth factor stimulates proliferation and confers Trastuzumab resistance to Her-2-overexpressing breast cancer cells," Clin Cancer Res. Jul. 15, 2006, vol. 12, pp. 4192-4199.

C. Landry, et al., Expression of Oligodendrocytic mRNAs in Glial Tumors: Changes Associated with Tumor Grade and Extent of Neoplastic Infiltration[1], Cancer Research, Sep. 15, 1997, vol. 57, pp. 4098-4104.

L. M. Liau, et al., "Identification of a Human Glioma-associated Growth Factor Gene, granulin, Using Differential Immuno-absorption[1]," Cancer Research, Mar. 1, 2000, vol. 60, pp. 1353-1360.

S. Lee, et al., "Enhanced Sensitization to Taxol-induced Apoptosis by Herceptin Pretreatment in ErbB2-overexpressing Breast Cancer Cells[1]," Cancer Research, Oct. 15, 2002, vol. 62, pp. 5703-5710.

R. Lu et al., "Stimulation of PC cell-derived growth factor (epithelin/granulin precursor) expression by estradiol in human breast cancer cells," Biochem Biophys Res Commun., Mar. 5, 1999, vol. 256, No. 1, pp. 204-207.

R. Lu et al., "Mediation of estrogen mitogenic effect in human breast cancer MCF-7 cells by PC-cell-derived growth factor (PCDGF/granulin precursor)," Proc Natl Acad Sci USA, Jan. 2001, vol. 98, No. 1, pp. 142-147.

R. Lu et al., "Resveratrol, a natural product derived from grape, exhibits antiestrogenic activity and inhibits the growth of human breast cancer cells," J Cell Physiol., Jun. 1999, vol. 179, No. 3, pp. 297-304.

G. Monami, et al., "Proepithelin Regulates Prostate Cancer Cell Biology by Promoting Cell Growth, Migration, and Anchorage-Independent Growth", Am J. Pathol., Mar. 2009, vol. 174, No. 3, pp. 1037-1047.

CX Pan et al., "PC cell-derived growth factor expression in prostatic intraepithelial neoplasia and prostatic adenocarcinoma," Clin Cancer Res., Feb. 15, 2004, vol. 10, No. 4, pp. 1333-1337.

G. Serrero, "Autocrine growth factor revisited: PC-cell-derived growth factor (progranulin), a critical player in breast cancer tumorigenesis," Biochem Biophys Res Commun., Aug. 29, 2003, vol. 3, pp. 409-413.

G. Serrero, "Endocrine and autocrine control of growth and differentiation of teratoma-derived cell lines," Prog. Clin. Bio. Res., 1986, vol. 226, pp. 191-204.

G. Serrero, "Expression of PC cell-derived growth factor in benign and malignant human breast epithelium," Hum Pathol., Nov. 2003, vol. 34, No. 11, pp. 1148-1154.

G. Serrero, et al., IHC Study of a novel marker of infiltrating ductal carcinoma, The third Era of Hope meeting for the Department of Defense (DOD) Breast Cancer Research Program (BCRP) held Sep. 25-28, 2002.

W. Tangkeangsirisin et al., "PC cell-derived growth factor (PCDGF/GP88, progranulin) stimulates migration, invasiveness and VEGF expression in breast cancer cells," Carcinogenesis, Sep. 25, 2004, vol. 9, pp. 1587-1592.

W. Tangkeangsirisin et al., "PC cell-derived growth factor mediates tamoxifen resistance and promote tumor growth of human breast cancer cell," Cancer Res. Mar. 1, 2004, vol. 64, No. 5, pp. 1737-1743.

H.E. Turner, et al., "Expression analysis of cyclins in pituitary adenomas and the normal pituitary gland," Clinical Endocrinology, (2000), vol. 53, pp. 337-344.

W. Wang et al., "PC cell-derived growth factor confers resistance to dexamethasone and promotes tumorigenesis in human multiple myeloma," Clin Cancer Res. Jan. 1, 2006, vol. 12, No. 1, pp. 49-56.

W. Wang et al., "PC-Cell Derived Growth Factor (PCDG, progranulin) Expression and Action in Human Multiple Myelomas," Proceedings of American Association for Cancer Research, Mar. 2001, vol. 42, p. 835.

W. Wang et al., "PC cell-derived growth factor (granulin precursor) expression and action in human multiple myeloma," Clin Cancer Res., Jun. 2003, vol. 9, No. 6, pp. 2221-2228.

X. Xia et al., "Identification of cell surface binding sites for PC cell-derived growth factor, PCDGF, (epithelin/granulin precursor) on epithelial cells and fibroblasts," Biochem Biophys Res Commun, Apr. 17, 1998, vol. 245, No. 2, pp. 539-543.

T. Zanocco-Marani, et al., "Biological Activities and Signaling Pathways of the Granulin/Epithelin Precursor," Cancer Research, Oct. 15, 1999, vol. 59, No. 20, pp. 5331-5340.

International Search Resort mailed Aug. 19, 2004; Appln. No. PCT/US2003/036792.

Serroro-Dave, G., Study of Teratoma-Derived Adipogenic Cell Line 1246 and Isolation of an Insulin-Independent Variant in Serum-Free Medium, Cancer Center, University of California, pp. 366-376, Oct. 7, 1982.

* cited by examiner

6G8 staining of normal and breast cancer tissues

Normal tissue No staining

AUTOCRINE GROWTH FACTOR RECEPTOR ANTIBODIES AND METHODS

This application is a continuation of U.S. application Ser. No. 10/298,540 filed Nov. 19, 2002, which is now U.S. Pat. No. 7,411,045, issued Aug. 12, 2008, and claims priority to provisional application Ser. No. 60/427,220 filed Nov. 19, 2002, the entire contents of both of which are incorporated by reference herein.

BACKGROUND OF THE INVENTION

PC-cell-derived growth factor ("PCDGF") is an 88-kDa glycoprotein autocrine growth factor expressed in a tightly regulated fashion in normal cells but overexpressed and unregulated in tumorigenic cells. Inhibition of PCDGF expression or activity inhibits the growth of tumorigenic cells. PCDGF is composed of a 68-KDa protein core and a 20-KDa carbohydrate moiety. PCDGF belongs to a novel family of double cysteine rich polypeptides and was originally isolated from the culture medium of the highly tumorigenic mouse teratoma-derived cell line PC. PCDGF has been shown to be overexpressed in mouse and human tumors including liver, kidney, breast, bone, bone marrow, testes, brain, ovary, skin, and lung.

Amino-acid and cDNA sequencing indicated that PCDGF is identical to the precursor of epithelins/granulins first purified as 6 KDa double cysteine-rich polypeptides from rat kidney or human granulocyte extracts. The granulin/epithelin precursor was previously thought to be inactive. See U.S. Pat. No. 5,416,192. However, Serrero et al. demonstrated that PCDGF is a highly active, tumorigenic protein associated with a variety of tumor cell types. See U.S. Pat. No. 6,309,826. The degree of overexpression of PCDGF positively correlates with the degree of tumorigenicity of cells. Id.

PCDGF is a growth modulator for a variety of cell lines, including fibroblasts, PC cells, and mammary epithelial cells. Comparison of the expression of PCDGF in the highly tumorigenic PC cells and in parent 1246 cells demonstrated that PCDGF expression was very low in the non-tumorigenic cells and was overexpressed in the highly tumorigenic cells. The same result was observed in human breast carcinomas where PCDGF expression was very low in non-tumorigenic mammary epithelial cells and increased in breast carcinoma cells.

PCDGF antagonists (e.g., anti-PCDGF antibodies and PCDGF antisense nucleic acids) inhibit or interfere with the activity of PCDGF and with the growth of tumorigenic cells. Zhang, H., and G. Serrero, 1998, *PNAS* 95, no. 24:14202; Lu, R., and G. Serrero, 2000, *PNAS* 97, no. 8:3993. In both teratoma-derived cells and breast cancer cells, PCDGF activity was inhibited by treating the cells with an anti-PCDGF neutralizing antibody or by transfecting the cells with an antisense PCDGF cDNA. Treatment of cells with PCDGF antagonists in teratoma cells or breast carcinoma cells completely inhibited cell proliferation and tumorigenesis in vivo. Id.

Antibodies are specialized proteins capable of binding a target molecule with great specificity. Originally identified as naturally produced protein products of the animal immune system, antibodies function as a primary arm of the immune system by binding to and facilitating clearance of microorganisms and other foreign substances from the body. Antibodies, also known as immunoglobulins (Ig), are generally formed from two "light" chains and two "heavy" chains. The carboxy terminus of the chains forms the constant or Fc region of the antibody while the amino terminus forms the variable or antigen-binding domain. There are at least five isotype categories of antibodies: IgG, IgE, IgA, IgM, and IgD. Each Ig isotype interacts with different effector cells resulting in different biological activities. For example, IgG marks foreign antigens for clearance by white blood cells (e.g., T cells) while IgE, located on the surface of mast cells, triggers allergic responses to particular antigens.

Animal models for generating antibodies are useful for making large quantities of antibodies directed to a desired antigen. However, human immune responses against "foreign" antibodies limit the therapeutic usefulness of antibodies developed in animals. "Humanized" antibodies substitute the complementarity determining regions ("CDRs") of animal antibodies with human CDRs resulting in a greatly reduced immune response in humans to the "foreign" antibody. See, e.g., Winter (British Application Number GB2188538A).

An anti-idiotypic antibody ("anti-IdAb") is an antibody that recognizes unique determinants generally associated with the antigen-binding site of an antibody. An anti-IdAb can be prepared by immunizing an animal of the same species and genetic type (e.g., mouse strain) as the source of the mAb with the mAb to which an anti-IdAb is being prepared. The immunized animal will recognize and respond to the idiotypic determinants of the immunizing antibody by producing antibody to these idiotypic determinants (the anti-IdAb). The anti-IdAb may also be used as an immunogen to produce an immune response in yet another animal, producing a so-called anti-anti-IdAb. The anti-anti-IdAb may be epitopically identical to the original mAb which induced the anti-IdAb. Thus, antibodies directed to the idiotypic determinants of an mAb can be used to generate antibodies of identical specificity to the original InAb.

U.S. Pat. No. 6,309,826 refers to the existence of PCDGF receptors on cell surfaces of several cell lines, including the mammary epithelial cell line C57MG, the 1246 and PC cell lines, and the mink lung epithelial cell line CCL64. In these studies, the PCDGF receptor was detected by binding labeled PCDGF to the PCDGF receptor and detecting the presence of PCDGF bound to its receptor on the cell surface. What is needed are PCDGF receptor antibodies and methods for binding to cell surfaces to interfere with the activity of the PCDGF receptor and the tumor promoting activity of PCDGF.

BRIEF SUMMARY OF THE INVENTION

The present invention provides antitumor compositions capable of binding to the surface of a cell expressing the PCDGF receptor and interfering with the binding of PCDGF to the PCDGF receptor. We have discovered antibodies capable of binding to the PCDGF receptor to inhibit the biological activity of PCDGF including, but not limited to, tumor cell proliferation induced by PCDGF. Anti-PCDGF receptor antibodies and/or antibody fragments can be made by immunizing an animal with an anti-PCDGF antibody. The resulting anti-PCDGF receptor antibodies or antibody fragments can be used to reduce the proliferation of tumor cells in vitro and in vivo.

The invention provides, in one embodiment, antitumor compositions comprising an antibody or antibody fragment capable of binding to the surface of a cell expressing the PCDGF receptor and interfering with the binding of PCDGF to the PCDGF receptor. Another embodiment of the invention provides a composition comprising an anti-PCDGF receptor antibody attached to a cytotoxic molecule for delivering the cytotoxic molecule to cells expressing the PCDGF receptor. The antibody-cytotoxic molecule composition can be used to kill cells expressing the PCDGF receptor. Further embodiments of the invention provide methods for inhibiting tumor cell proliferation by contacting a tumorigenic cell with an effective amount of anti-PCDGF receptor antibody.

Additional embodiments and advantages of the present invention will be set forth in part in the description that follows, and in part will be obvious from the description, or may be learned through the practice of the invention. The objects and advantages of the invention will be attained by means of the instrumentalities and combinations particularly pointed out in the appended claims.

DETAILED DESCRIPTION OF THE INVENTION

PCDGF is a highly tumorigenic autocrine growth factor and causative agent for a wide variety of tumors. As described in U.S. Pat. No. 6,309,826, incorporated by reference herein in its entirety, overexpression of PCDGF leads to uncontrolled cell growth and increased tumorigenesis. The degree of PCDGF overexpression directly correlates with the degree of cellular tumorigenicity. Cells overexpressing PCDGF do not require external signals to maintain uncontrolled cell growth. Loss of regulated cell growth, such as a loss in responsiveness to insulin and/or estrogen, leads to increased malignancy and excessive unregulated cell growth. Development of methods and compositions that interfere with the tumorigenic activity of PCDGF is therefore of great interest for the treatment of cancer.

PCDGF antagonists, such as anti-PCDGF antibodies, interfere with the biological activity of PCDGF (e.g., tumorigenic activity) by binding PCDGF directly and preventing PCDGF from transmitting cell growth signals to a target cell (e.g., breast cancer cell). An anti-PCDGF antibody may bind the active site of PCDGF (e.g., the PCDGF receptor binding site) and prevent PCDGF from binding to its receptor. Alternatively, anti-PCDGF antibodies may bind to a site on PCDGF other than the active site, alter the conformation of the active site, and thus render PCDGF incapable of binding to its receptor. Anti-PCDGF antibodies include PCDGF neutralizing antibodies. "Neutralizing" antibodies have the ability to inhibit or block the normal biological activity of PCDGF, including PCDGF's ability to stimulate cell proliferation, increase cell survival, block apoptosis, or induce tumor growth in animals and in humans.

We have found that another useful target for interfering with the biological activity of PCDGF is the PCDGF receptor. The term "receptor" refers to a protein capable of transmitting signals from one ligand to another ligand. Generally, receptors are transmembrane proteins having extracellular, transmembrane, and intracellular domains. For example, a ligand, such as a growth factor, can bind to its receptor's extracellular domain, resulting in a receptor having an altered conformation. The intracellular domain, having an altered conformation, is now capable of binding to an intracellular molecule, which transmits the signal to another molecule in another cellular location (e.g., a nuclear transcription factor). Interfering with the biological activity of a receptor breaks the signal chain from the extracellular ligand to the intracellular ligand. Alternatively, molecules that target the receptor can be designed to inactivate or kill a cell expressing a particular receptor (e.g., cytotoxic molecules linked to anti-receptor antibodies).

We first demonstrated the existence of the PCDGF receptor in U.S. Pat. No. 6,309,826 using the mink lung epithelial cell line CCL64. Scatchard analysis of binding of 125I1-PCDGF revealed the presence of two classes of cell surface receptors: a high affinity class with a Kd of $4.3+-1.5 \times 10^{-11}$ M and 560+−170 sites/cell, and a low affinity class of receptors with a Kd of $3.9+-1.9 \times 10^{-9}$ M and 17,000+−5900 sites/cell. Cross-linking studies and autoradiographic analysis revealed the presence of one major cross-linked band with a molecular weight of 190-195 KDa, corresponding to a molecular weight for the unbound receptor of about 110 KDa for the major band. We have shown that PCDGF receptors belong to the tyrosine kinase family of receptors. Upon binding of PCDGF to the cell surface, the PCDGF receptor is activated by phosphorylation on tyrosine residues, resulting in phosphorylation of several signaling molecules, including IRS-1, SHC, and Grb2, and leading to activation of MAP kinase ERK-2.

The term antibody herein includes but is not limited to human and non-human polyclonal antibodies, human and non-human monoclonal antibodies (mAbs), chimeric antibodies, anti-idiotypic antibodies (anti-IdAb), neutralizing antibodies, non-neutralizing antibodies, and humanized antibodies. Polyclonal antibodies are heterogeneous populations of antibody molecules derived either from sera of animals immunized with an antigen or from chicken eggs. Monoclonal antibodies ("mAbs") are substantially homogeneous populations of antibodies to specific antigens. mAbs may be obtained by any suitable method. Such antibodies may be of any immunological class including IgG, IgM, IgE, IgA, IgD and any subclass thereof. The hybridoma producing human and non-human antibodies to the PCDGF receptor may be cultivated in vitro or in vivo. For production of a large amount of mAbs, in vivo is the presently preferred method of production. Briefly, cells from the individual hybridomas can be injected intraperitoneally into pristane primed Balb/c mice or Nude mice to produce ascites fluid containing high concentrations of the desired InAbs. mAbs may be purified from such ascites fluids or from culture supernatants using various chromatography methods known in the art.

Human monoclonal Ab to human PCDGF receptor can be prepared by immunizing transgenic mice expressing human immunoglobulin genes. Hybridomas produced by using lymphocytes from these transgenic animals will produce human immunoglobulin instead of mouse immunoglobulin. Since most monoclonal antibodies are derived from murine and other non-human sources, their clinical efficacy may be relatively limited due to the immunogenicity of rodent mAbs administered to humans, weak recruitment of effector function, and rapid clearance from serum. To circumvent these problems, the antigen-binding properties of murine antibodies can be conferred to human antibodies through a process called humanization. A humanized antibody contains the amino-acid sequences for at least 6 complementarity-determining regions (CDRs) of the parent murine mAb which are grafted onto a human antibody framework. The low content of non-human sequences in humanized antibodies (around 5%) has proven effective in both reducing the immunogenicity and prolonging the serum half life in humans. Methods of using monovalent phage display and combinatorial library strategy for humanization of monoclonal antibodies are known in the art. Humanized antibodies and human antibodies developed with transgenic animals as described above are of therapeutic use for diseases including cancer.

Chimeric antibodies have different portions from different animal species. For example, a chimeric antibody might have a variable region from a murine mAb and a human immunoglobulin constant region. Chimeric antibodies and methods for their production are also known to those skilled in the art.

Hybridoma supernatants may be screened for the presence of antibody specific for PCDGF receptor by any number of immunoassays including dot blots and standard immunoassays (EIA or ELISA) which are well known in the art. Once a supernatant has been identified as having an antibody of interest, it may be further screened by Western blotting to identify the size of the antigen to which the antibody binds. One of ordinary skill in the art may prepare and screen such hybridomas without undue experimentation in order to obtain a desired polyclonal or nab given the teachings herein.

In a preferred embodiment of the invention, anti-PCDGF receptor antibodies can be made by immunizing animals with PCDGF, permitting the animals to produce anti-ID PCDGF antibodies, and utilizing spleen cells from the immunized mice to produce hybridoma cell lines capable of secreting anti-PCDGF receptor antibodies. See e.g., U.S. Pat. No. 5,144,010 hereby incorporated by reference in its entirety. For example, anti-PCDGF receptor antibodies can be made by (a) injecting animals (e.g., mice, rabbits) with an effective amount of PCDGF to elicit an immune response; (b) periodically collecting blood samples from the animals; (c) screening the blood samples to determine if the animals are making antibodies directed to PCDGF and/or antibodies to the PCDGF receptor; (d) making hybridoma cells (e.g., fusing spleen cells from the animals with myeloma cells) after the animals cease making anti-PCDGF antibodies and continue to make anti-PCDGF receptor antibodies; (e) purifying the anti-PCDGF receptor antibodies produced by the selected hybridoma cell lines.

Initially, the animals respond by producing anti-PCDGF antibodies. About 15 to 30 days after the appearance of high-titered anti-PCDGF IgG, the animals produce antibodies to the anti-PCDGF antibodies and stop or reduce the production of anti-PCDGF antibodies. For example, an animal (e.g., mouse, rat, rabbit) can be injected with about 10 to about 100 µg of purified PCDGF (e.g., recombinant PCDGF). The animals can be injected with PCDGF about three to five times over the course of about 30 to 60 days. The titer of anti-Id PCDGF antibodies can be monitored by screening blood samples (e.g., tail bleeds) against cells expressing a high level of PCDGF receptors (e.g., C57MG, 1246, PC-cells, CCL64). About 15 to 30 days after high titer anti-PCDGF antibodies are formed, anti-Id antibodies will be produced by the animals. Spleen cells from immunized mice can be used to produce hybridomas secreting anti-PCDGF receptor antibodies. Anti-PCDGF receptor antibodies can be purified from the hybridoma cells by several well-established methods including, but not limited to, purification using Protein A or Protein G affinity chromatography columns.

Alternatively, anti-PCDGF antibodies may be used to induce human and non-human anti-Id Abs in suitable animals. Animals can be immunized with anti-PCDGF antibodies and will produce antibodies to the anti-PCDGF antibodies. Anti-PCDGF antibodies that can be used to make anti-idiotypic anti-PCDGF receptor antibodies include 6B3, 6B2, 6C12, 5B4, 5G6, 4D1, 3F8, 3F5, 3F4, 3G2, and 2A5. Hybridoma cell lines producing these anti-PCDGF antibodies have been deposited with the American Type Culture Collection (ATCC), 10801 University Blvd., Manassas, Va. 20110-2209, and have the following designations: 6B3 hybridoma cell line (ATCC Accession Number PTA-5262), 6B2 hybridoma cell line (ATCC Accession Number PTA-5261), 6C12 hybridoma cell line (ATCC Accession Number PTA-5597), 5B4 hybridoma cell line (ATCC Accession Number PTA-5260), 5G6 hybridoma cell line (ATCC Accession Number PTA-5595), 4D1 hybridoma cell line (ATCC Accession Number PTA-5593), 3F8 hybridoma cell line (ATCC Accession Number PTA-5591), 3F5 hybridoma cell line (ATCC Accession Number PTA-5259), 3F4 hybridoma cell line (ATCC Accession Number PTA-5590), 3G2 hybridoma cell line (ATCC Accession Number PTA-5592), and 2A5 hybridoma cell line (ATCC Accession Number PTA-5589). All restrictions imposed by the depositor on the availability to the public of the deposited material will be irrevocably removed upon the granting of the patent. Each of the above referenced hybridoma cells lines can be induced to express the designated anti-PCDGF antibody by maintaining the cell line in DMEM plus 10% FBS until the desired quantities of anti-PCDGF antibodies are secreted into the cell culture medium. Anti-PCDGF antibodies can be purified from the cell culture medium by well established methods such as purification using Protein A or Protein G affinity chromatography columns. Such anti-PCDGF antibodies can be used, for example, to detect the presence of PCDGF, diagnose tumorigenicity, and/or inhibit tumor cell proliferation as described in U.S. Pat. No. 6,309,826.

Cells overexpressing the PCDGF receptor can also be used as antigens to induce human and non-human anti-PCDGF antibodies in animals. Animals can be immunized with whole cells or cell fractions (e.g., membranes) overexpressing the PCDGF receptor (e.g., C57MG, 1246, PC-cells, CCL64 cells). For example, 1 to 10 million cells can be injected into suitable animals. The titer of anti-PCDGF antibodies can be monitored by screening blood samples (e.g., tail bleeds) against cells expressing a high level of PCDGF receptors (e.g., C57MG, 1246, PC-cells, CCL64). Spleen cells from immunized mice can be used to produce hybridomas secreting anti-PCDGF receptor antibodies. The culture supernatants from the hybridomas can be screened against cancer cells by enzyme-linked immunoabsorbance assay (ELISA). Anti-PCDGF receptor antibodies will compete with purified PCDGF for cell surface binding to cells overexpressing the PCDGF receptor. The selected anti-PCDGF receptor antibodies can be purified from the hybridoma cells by several well-established methods including, but not limited to, purification using Protein A or Protein G affinity chromatography columns.

The term antibody is also meant to include both intact molecules as well as fragments thereof such as, for example, Fab and F(ab')2, which are capable of binding to the antigen. Fab and F(ab')2 fragments lack the Fc fragment of intact antibody, clear more rapidly from the circulation, and may have less non-specific tissue binding than an intact antibody. Such fragments are typically produced by proteolytic cleavage, using enzymes such as papain (to generate Fab fragments) and pepsin (to generate F(ab')2 fragments).

One embodiment of the present invention provides antitumor compositions which include an antibody or antibody fragment capable of binding to the surface of a cell expressing the PCDGF receptor and interfering with the binding of PCDGF to the PCDGF receptor. The anti-PCDGF receptor antibody may be an anti-idiotypic antibody. Anti-PCDGF receptor antibodies 6G8, 4H1, 2C1, 5A8, 2F8, and 2B12 are examples of anti-idiotypic antibodies made by immunizing mice with PCDGF. Hybridoma cell lines producing these anti-PCDGF receptor antibodies have been deposited with the American Type Culture Collection (ATCC) and have the following designations: 6G8 (ATCC Accession Number PTA-5263), and 5A8 (ATCC Accession Number PTA-5594). The above referenced hybridoma cells lines can be induced by maintaining the cell line in DMEM plus 10% FBS until the desired amount of anti-PCDGF receptor antibody is secreted from the cells into the cell culture medium. Anti-PCDGF receptor antibody can be purified from the cell culture medium by well established methods such as, but not limited to affinity chromatography using Protein A or Protein G columns. Other anti-idiotypic antibodies can be prepared as described above.

As used herein, the term "binding" refers to specific or non-specific interactions between one molecule and another molecule. Examples of "binding" include, but are not limited to, the direct interaction between the antigen binding site of an antibody and the antigenic determinant of its antigen or to non-specific associations between molecules (e.g., co-localization, electrostatic interactions, and phase interactions).

The term "contacting" means providing anti-PCDGF receptor antibody to the environment of a cell whereby the anti-PCDGF receptor antibody is capable of binding to a cell having a PCDGF receptor on its surface. For example, injecting anti-PCDGF receptor antibody directly into a tumor such that the antibody diffuses into the tumor is considered "contacting" the cells with the anti-PCDGF receptor antibody whether the anti-PCDGF receptor antibody actually binds to its receptor on the surface of the cell or not.

Administration of Anti-PCDGF Receptor Antibody and Compositions

Anti-PCDGF receptor antibodies can be provided to cells both in vitro and in vivo. For in vitro applications, anti-PCDGF receptor antibodies can be added to cell culture medium at concentrations typically ranging from 0.01 ng to about 500 μg/ml and preferably from about 10 ng to about 100 μg/ml. Antibody may be administered alone or in conjunction with other therapeutics directed to the same disease. Cells can also be transfected with DNA or RNA encoding anti-PCDGF receptor antibodies or antibody fragments or vectors containing such DNA or RNA sequences. Transfected cells can be induced to make anti-PCDGF receptor antibodies or antibody fragments using any suitable technique (e.g., inducible promoter, and multiple plasmid copies).

Anti-PCDGF receptor antibody compositions can also be administered to cells using ex vivo techniques. Tumorigenic or normal cells can be removed from a subject (e.g., human, dog, cow, goat, mouse, rat, rabbit, horse, or chicken) and grown in culture. The cells can be transfected with DNA or RNA encoding anti-PCDGF receptor antibodies and induced to produce anti-PCDGF receptor antibodies. The transfected cells can then be reintroduced into the subject and produce anti-PCDGF receptor antibodies or antibody fragments in order to inhibit the activity of PCDGF and reduce tumor cell proliferation.

For in vivo applications, anti-PCDGF receptor antibody compositions can be provided to a subject by a variety of administration routes and dosage forms. A subject, preferably a human subject, suffering from disease associated with increased PCDGF expression is treated with an anti-PCDGF receptor antibody or fragment. Alternatively, a subject's cells are transfected with a polynucleotide encoding an anti-PCDGF receptor antibody or fragment. A typical regimen comprises administration of an effective amount of the anti-PCDGF receptor antibody over a period of one or several weeks and including between about one and six months. The antibody of the present invention may be administered by any means that achieves its intended purpose. For example, administration may be by various routes including but not limited to subcutaneous, intravenous, intradermal, intramuscular, intraperitoneal and oral. Parenteral administration can be by bolus injection or by gradual perfusion over time. Preparations for parenteral administration include sterile aqueous or nonaqueous solutions, suspensions and emulsions, which may contain auxiliary agents or excipients known in the art. Pharmaceutical compositions such as tablets and capsules can also be prepared according to routine methods. It is understood that the dosage will be dependent upon the age, sex and weight of the recipient, kind of concurrent treatment, if any, frequency of treatment and the nature of the effect desired. The ranges of effective doses provided below are not intended to limit the invention and merely represent illustrative dose ranges. However the most preferred dosage will be tailored to the individual subject as is understood and determinable by one of ordinary skill in the art given the teachings herein. The total dose required for each treatment may be administered by multiple doses or in a single dose. Effective amounts of antibody are typically from about 0.01 ng to about 500 μg/ml and preferably from about 10 ng to about 100 μg/ml. Antibody may be administered alone or in conjunction with other therapeutics directed to the same disease.

Figure 1:
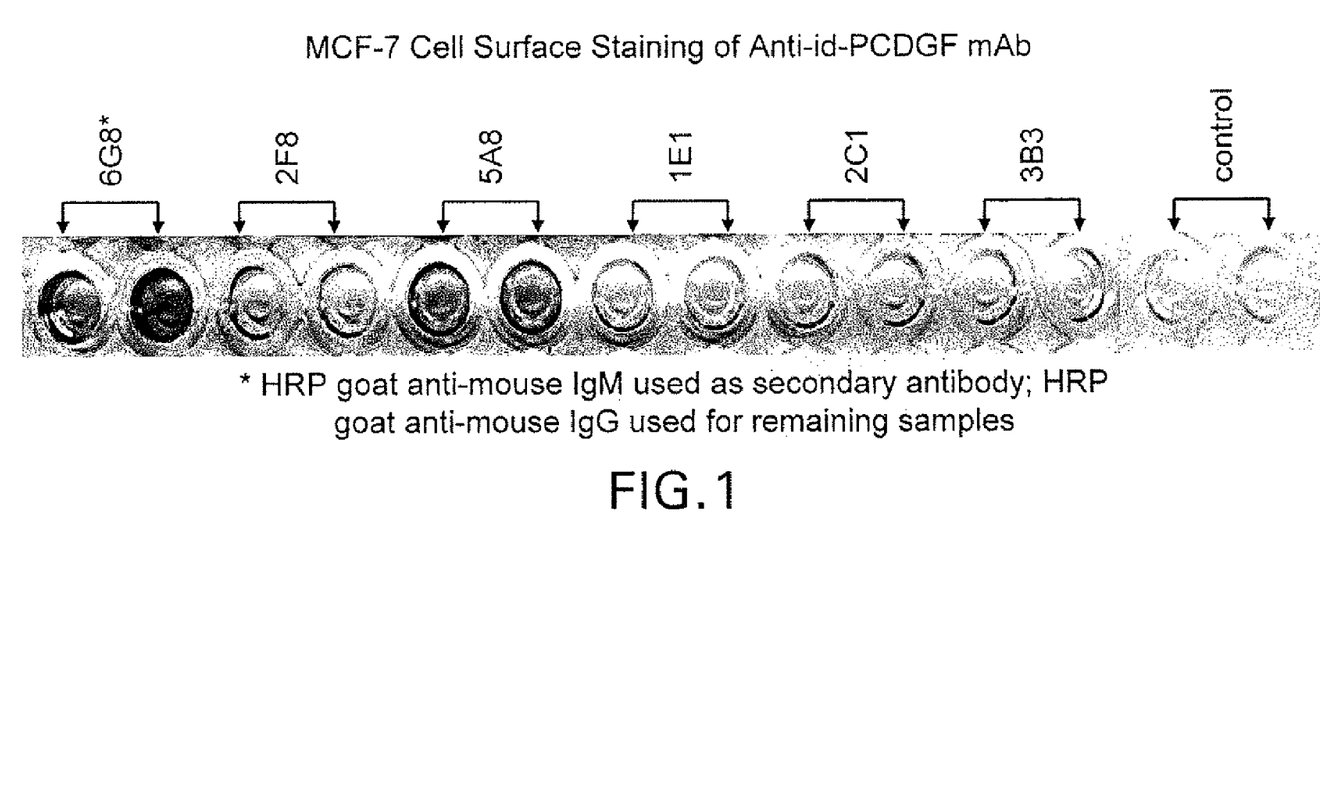
FIG. 1 shows that anti-PCDGF receptor antibodies bind to the surface of MCF-7 human breast cancer cells. Antibody 6G8, an IgM antibody, exhibited the strongest binding to the cell surface (lanes 1 and 2).
Figure 2:
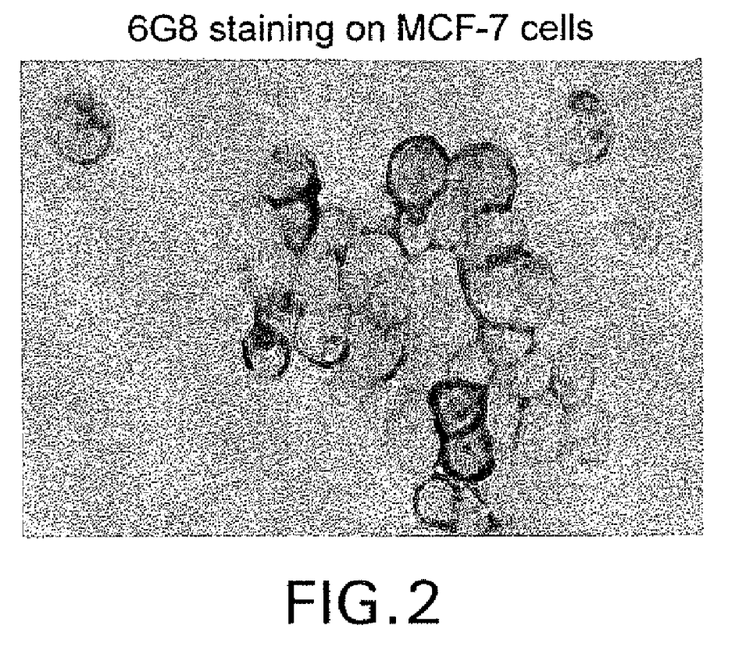
FIG. 2 shows MCF-7 cells immunostained with anti-PCDGF receptor antibody 6G8.

As shown in FIGS. 1 and 2, anti-PCDGF receptor antibodies bind to the surface of MCF-7 breast cancer cells. In an immunostaining assay, purified anti-PCDGF receptor antibodies designated as 6G8, 2F8, 5A8, E11, 2C1, and 3B3 were added to MCF-7 cells seeded in 96 well plates, incubated with a secondary antibody linked to a horseradish peroxidase (HRP). The results show the anti-PCDGF receptor antibodies bind strongly to the surface of the MCF-7 cells (FIG. 1). FIG. 2 shows that anti-PCDGF receptor antibodies stain the cell surface of MCF-7 cells.

Figure 3:
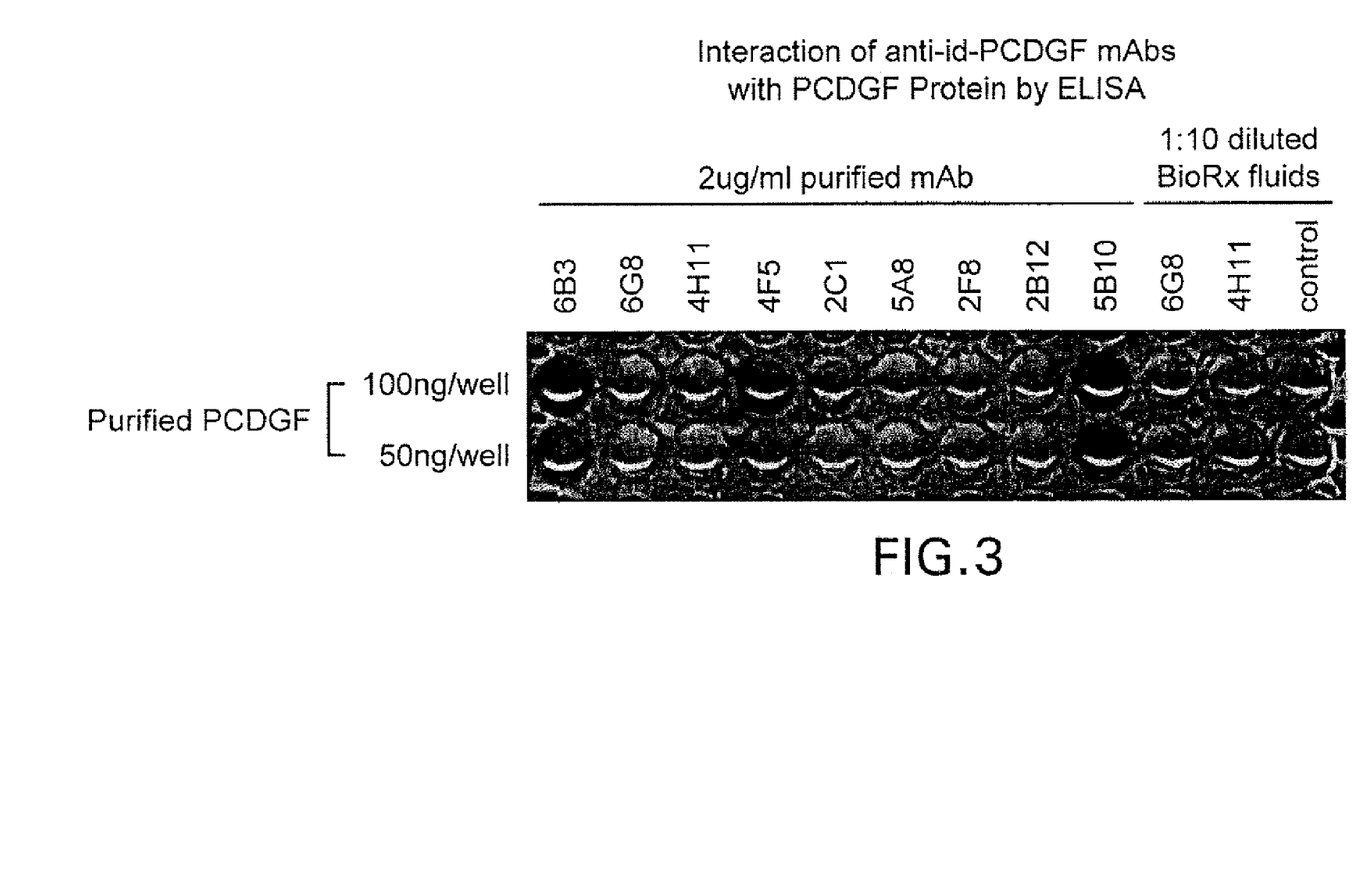
FIG. 3 shows that anti-PCDGF receptor antibodies 6G8, 4H11, and 5A8 do not react with PCDGF protein in an ELISA assay (Lanes 2, 3, and 6).

As shown in FIG. 3, anti-PCDGF receptor antibodies 6G8, 4H1, 2C1, 5A8, 2F8, and 2B12 do not bind to purified PCDGF in an ELISA (enzyme linked immunoabsorption assay). However, anti-PCDGF antibody 6B3 binds to PCDGF. Thus, anti-PCDGF receptor antibodies do not bind to PCDGF.

Anti-PCDGF Receptor Antibodies Block PCDGF-Induced Biological Functions

Figure 4:
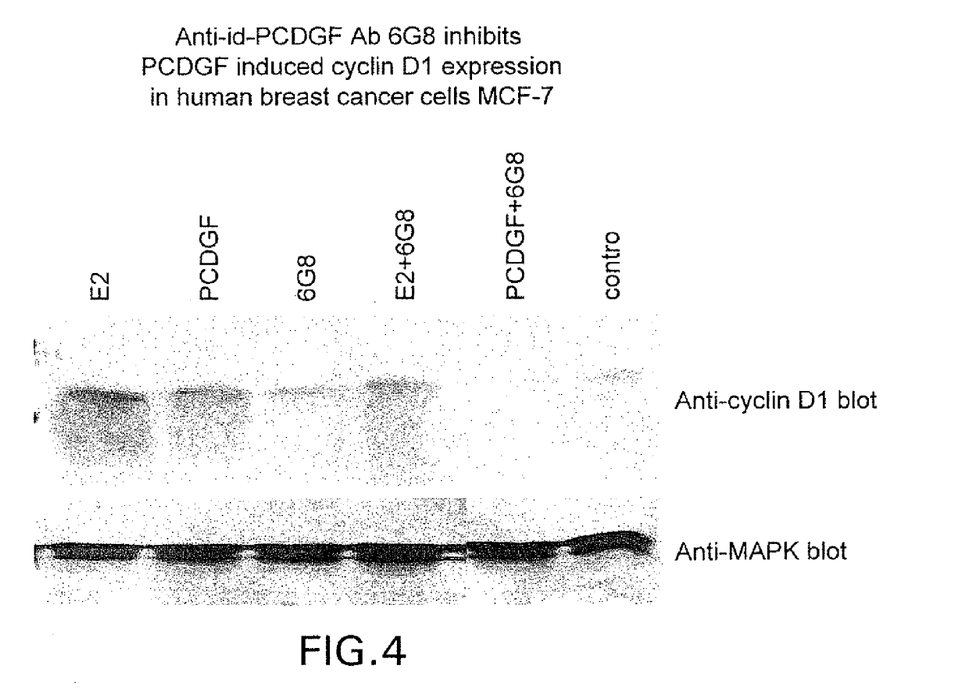
FIGS. 4 and 5 demonstrate that anti-PCDGF receptor antibodies and anti-PCDGF antibodies, respectively, block PCDGF-induced cyclin D1 expression.
Figure 5:
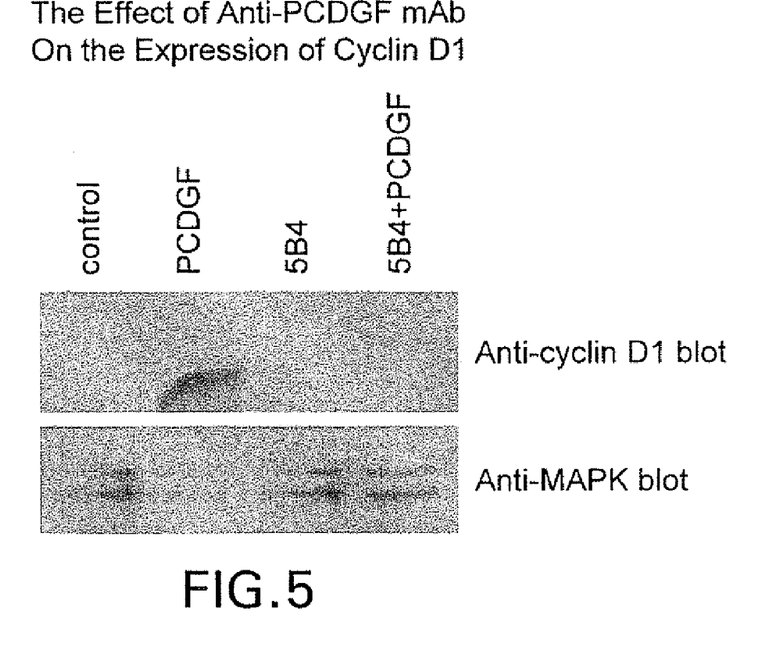
Figure 6:
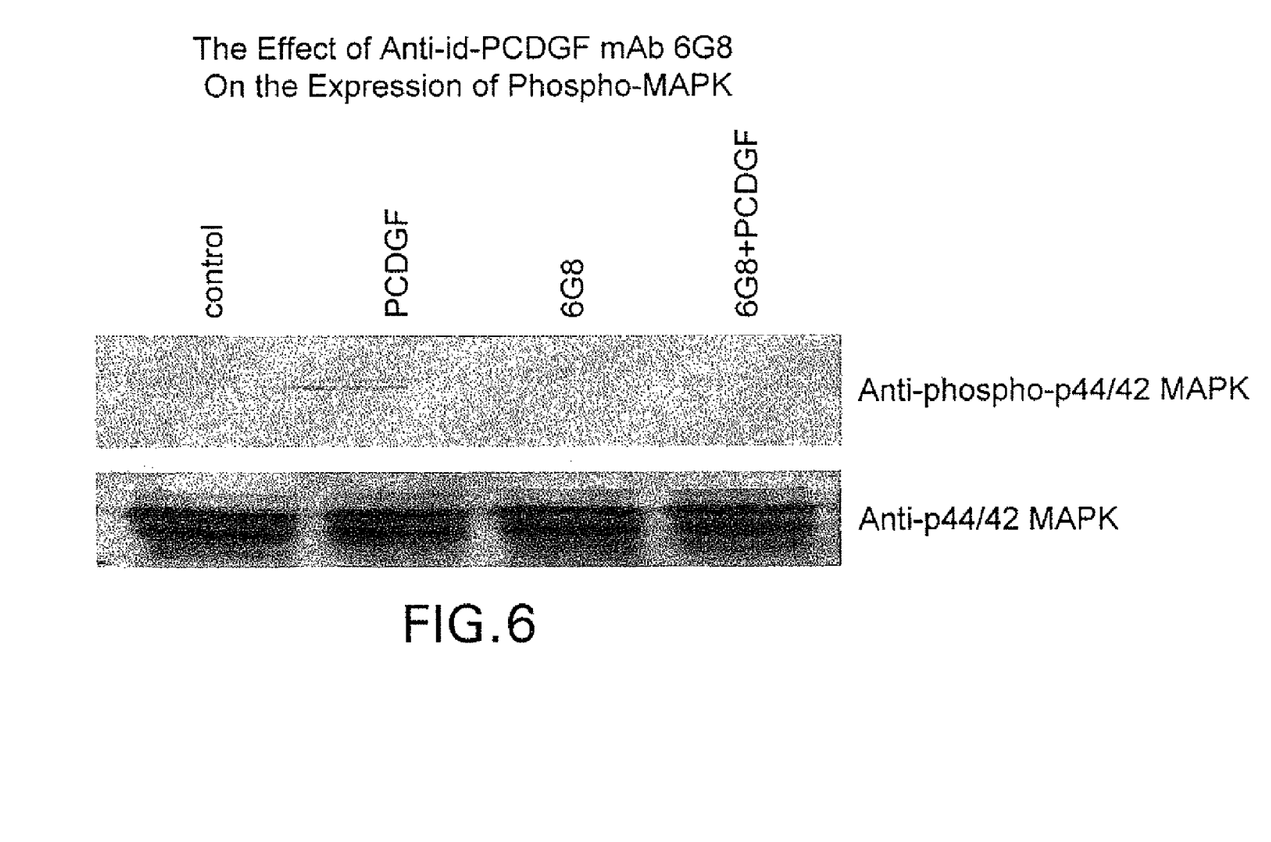
FIG. 6 shows that anti-PCDGF receptor antibodies block PCDGF-induced phosphorylation of MAPK.

In one embodiment, PCDGF receptor antibodies specifically block PCDGF-induced cyclin D1 expression. As shown in FIG. 4, both PCDGF and estradiol stimulate cyclin D1 expression in MCF-7 cells. Anti-PCDGF receptor antibody 6G8 specifically blocks PCDGF-induced cyclin D1 expression but not estradiol-induced cyclin D1 expression. Compare lanes 4 and 5 of FIG. 4. FIG. 5 shows that anti-PCDGF receptor antibody 5B4 specifically blocks PCDGF-induced cyclin D1 expression in MCF-7 cells. Anti-PCDGF receptor antibodies also block PCDGF-induced phosphorylation of MAPK. As shown in FIG. 6, Western blot analysis using anti-phospho-p44/p42 antibody shows that PCDGF induces phosphorylation of MAPK (lane 2). The addition of anti-PCDGF receptor antibody (e.g., 6G8) blocks PCDGF-induced phosphorylation of MAPK (lane 4). Anti-PCDGF antibody alone does not induce phosphorylation of MAPK.

While not wishing to be bound by theory, when anti-PCDGF receptor antibodies do not bind PCDGF (FIGS. 1 and 2), and bind to the cell surface to block PCDGF-induced biological activity (e.g., inducement of cyclin D1 and phosphorylation of MAPK), we believe that such anti-PCDGF receptor antibodies are specifically binding the PCDGF receptor.

Figure 7:
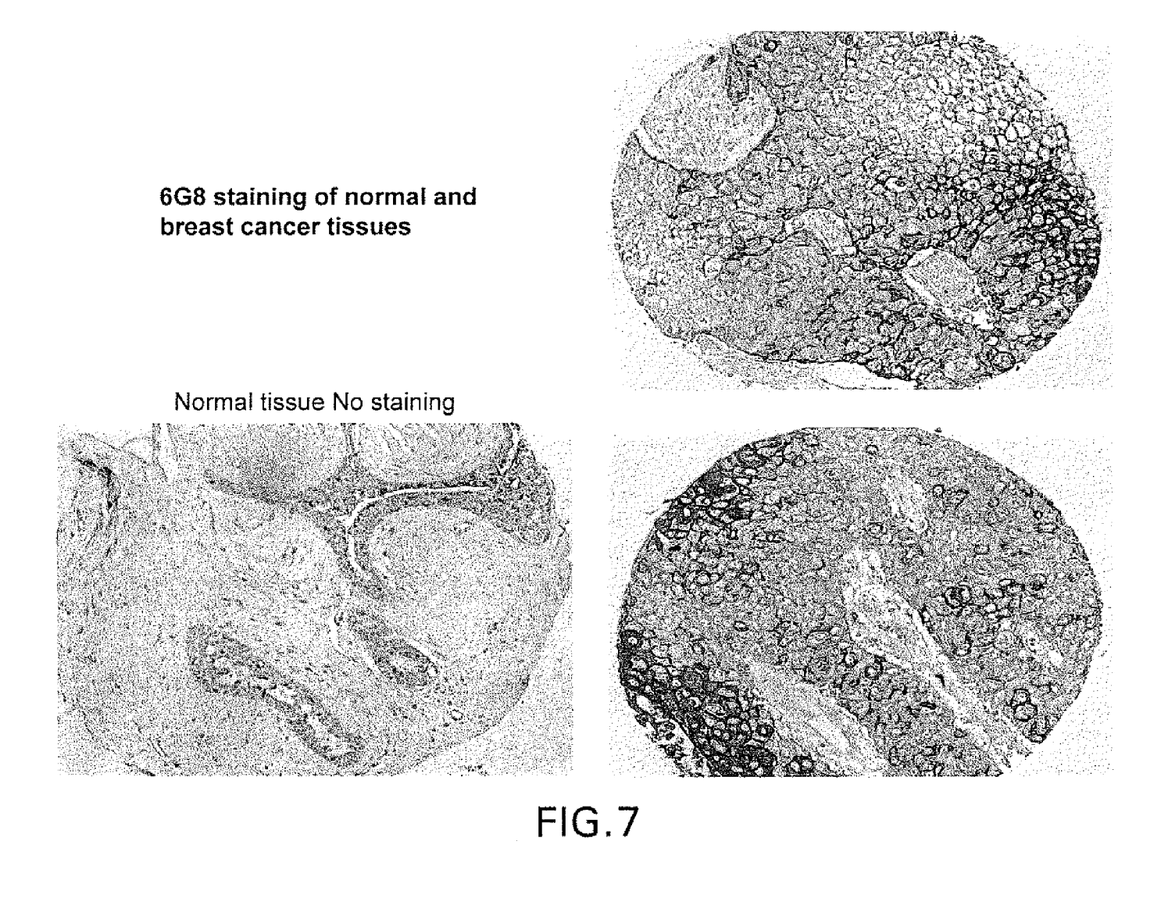
FIG. 7 shows immunostaining of breast cancer and normal breast tissue with anti-PCDGF receptor antibody 6G8. Anti-PCDGF receptor antibody 6G8 strongly stains breast cancer tissue, but does not significantly stain normal tissue.

Anti-PCDGF receptor antibodies are capable of binding to tumorigenic cells but not to normal cells. As shown in FIG. 7, anti-PCDGF receptor antibodies bind strongly to breast cancer tissue (panels B and C) but not to normal tissue (panel A) in an immunostaining protocol using 10 micrograms/ml of 6G8 anti-PCDGF receptor antibody. Thus, anti-PCDGF receptor antibodies can also be used to diagnose tumorigenicity by comparing the level of PCDGF receptor in a tissue sample or biopsy to the level of PCDGF receptor in normal tissue. Elevated levels of PCDGF receptor indicate the cells are tumorigenic.

Figure 8:
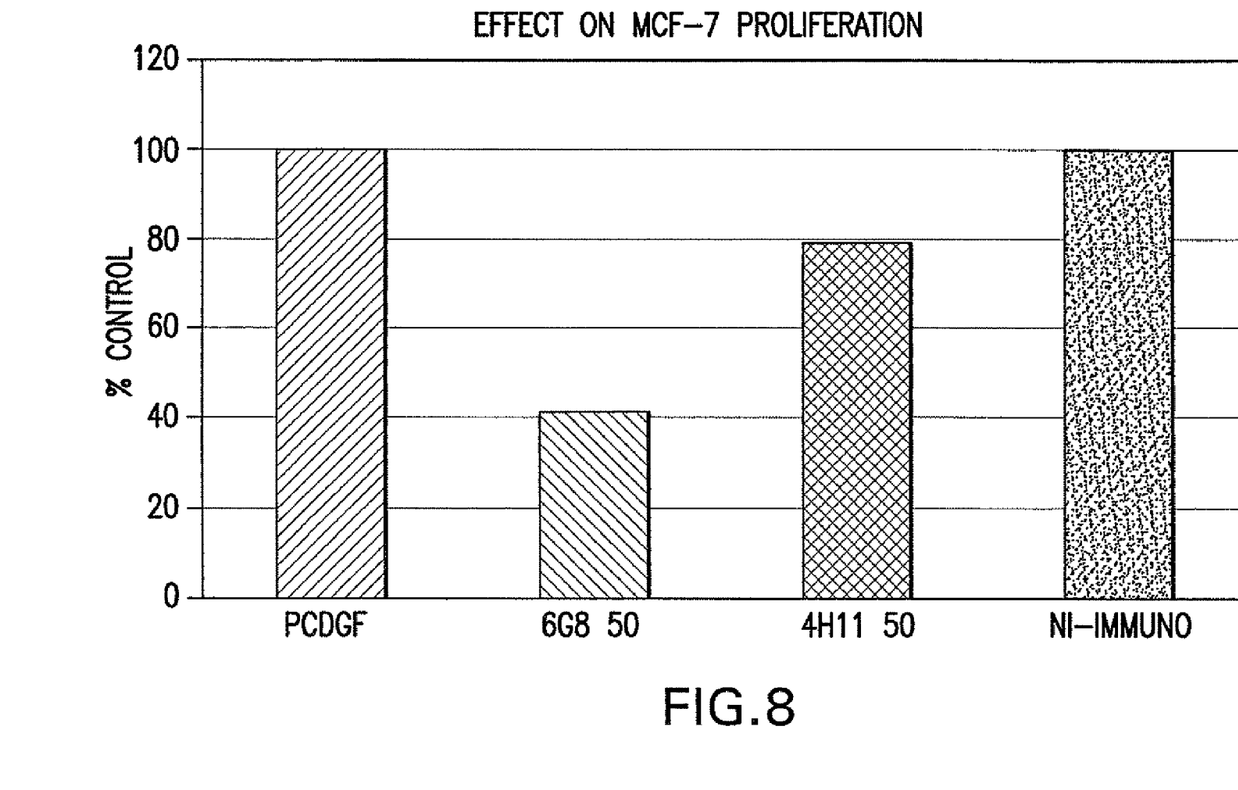
FIG. 8 shows the inhibiting effect of anti-PCDGF receptor antibodies on the proliferation of MCF-7 cells. Anti-PCDGF receptor antibodies 6G8 and 4H11 inhibited MCF-7 cell proliferation by up to about 60% (columns 2 and 3).

In accordance with a preferred embodiment of the invention, anti-PCDGF receptor antibodies are utilized to reduce the proliferation of tumorigenic cells. As shown in FIG. 8, anti-PCDGF receptor antibodies have been shown to reduce proliferation of human breast cancer cells by up to about 60% (6G8). Anti-PCDGF receptor antibodies are used in accordance with another embodiment of the invention to reduce the proliferation of tumorigenic cells by contacting the cells with an effective amount of anti-PCDGF receptor antibody. An effective amount of anti-PCDGF receptor antibody typically ranges from about 0.01 ng to about 500 µg/ml and preferably from about 10 ng to about 100 µg/ml. The "tumorigenic cells" includes, but are not limited to, cells derived from blood, cerebrospinal fluid, serum, plasma, urine, nipple aspirate, liver, kidney, breast, bone, bone marrow, testes, brain, ovary, skin, and lung.

It is to be understood that application of the teachings of the present invention to a specific problem or environment will be within the capability of one having ordinary skill in the art in light of the teachings contained herein. The present invention is more fully illustrated by the following non-limiting examples.

EXAMPLE 1

Cell Surface Staining of PCDGF Receptor Antibody on Human Breast Cancer MCF-7 Cell Line $1 \times 10^5$/well MCF-7 cells were seeded in 96 well plates and incubated at 37° C., in a 5% $CO_2$ incubator overnight. Purified anti-id-PCDGF mAbs 6G8, 2F8, E11, 2C1 and 3B2 were diluted in DMEM, 5% FBS medium at 50 µg/ml. 200 µl/well of each monoclonal antibody (mAb) was added in duplicate wells and incubated at room temperature for 1 hour. Cells were then washed three times in PBS and incubated with a goat anti-mouse IgG or IgM (for 6G8 only) conjugated to horseradish peroxidase ("HRP") at 1:2000 dilution for 1 hour. After an additional three washes in PBS, a TMB microwell component peroxidase substrate was added to each well. The plates were read in a plate reader set at a wavelength of 620 nanometers. Anti-PCDGF receptor antibodies stained the surface of the MCF-7 cells (FIG. 1).

Immunostaining of MCF-7 Cells With Anti-PCDGF Receptor Antibody

Fixed MCF-7 cells were blocked with 3% BSA/PBS and incubated with 10 µg/ml of anti-PCDGF receptor antibody 6G8 in 3% BSA/PBS for 1 hour at 25° C. After three washes, the cells were incubated with goat anti-mouse IgM conjugated with HRP for 1 hour at 25° C. After an additional wash, the cells were incubated with HRP substrate. MCF-7 cells were stained specifically with 6G8 (FIG. 2).

PCDGF Receptor Antibodies Stain Breast Cancer Tissue But Not Normal Tissue

Tissue sections from a normal breast (low left panel) and breast cancers (right up and low panels) were stained with 10 µg/ml of 6G8 mAb using immunohistochemistry techniques described above. No significant staining was observed with human normal breast tissue. However, anti-PCDGF receptor antibody 6G8 stained the cancer tissues specifically as shown in FIG. 7.

EXAMPLE 2

PCDGF Receptor Antibodies Which Do Not Bind To PCDGF

Purified PCDGF protein was diluted in PBS and coated onto 96 well ELISA plates at a concentration of 100 ng/well and 50 ng/well. The treated plates were incubated overnight at 4° C. After washing 3 times with PBS, the plate was blocked with 5% non-fat milk PBS for 1 hour at room temperature. 2 µg/ml purified or 1:10 diluted BioRx fluids of PCDGF receptor mAb was added to each well and incubated at room temperature for 1 hour. The plate was washed 3 times with PBS and incubated with HRP conjugated goat anti-mouse IgG secondary antibody for another hour. After an additional three washes in PBS, a TMB microwell 1 component peroxidase substrate was added to each well. The plates were read in a plate reader set at a wavelength of 620 nanometers. As shown in FIG. 3, the anti-PCDGF receptor antibodies did not bind PCDGF.

EXAMPLE 3

PCDGF Receptor Antibody 6G8 Inhibits PCDGF Induced Cyclin D1 Expression in Human Breast Cancer MCF-7 cells $2 \times 10^5$/ml MCF-7 cells were plated in 6 well plates in DME/F12 medium plus 5% FBS overnight. The cell culture medium was replaced with phenol-red free DMEM/F12 supplemented with 5% charcoal-stripped FBS and synchronized by treatment with 1 uM Tamoxifen for 48 hours. The cell culture medium was then replaced with serum free, phenol-red free DME/F12 and treated with either $10^{-9}$M estradiol (E2), 200 ng/ml PCDGF or 6G8 (50 µg/ml) alone or with E2 or PCDGF for 5 hours. After treatment, cells were lysed with RIPA buffer plus protease inhibitors. 60 µg of whole cell lysates were separated by 10% SDS-PAGE gel, and proteins were electrotransferred onto nitro-cellulose membranes. Western blot detection of cyclin D1 expression was performed using anti-cyclin D1/2 clone 5D4 monoclonal antibody (FIG. 4). As shown in FIG. 4, either PCDGF or E2 induced the expression of cyclin D1 expression in MCF-7 cells. Anti-PCDGF receptor antibody alone has no significant effect on cyclin D1 expression. However, addition of 6G8 inhibits cyclin D1 expression induced by either E2 or PCDGF.

EXAMPLE 4

The Effect of Anti-PCDGF Mab 5B4 on the Expression of Cyclin D1

$2 \times 10^5$/ml MCF-7 cells were plated in 6 well plates in DME/F12 medium plus 5% FBS overnight. The cell culture medium was replaced with phenol-red free DMEM/F12 supplemented with 5% charcoal-stripped FBS and synchronized by treatment with 1 uM Tamoxifen for 48 hours. The cell culture medium was then replaced with serum free, phenol-red free DME/F12 and treated with 200 ng/ml PCDGF or 5B4 (100 µg/ml) and 5B4 with PCDGF for 5 hours. After treatment, cells were lysed with RIPA buffer plus protein inhibitors. 60 µg of whole cell lysates were separated by 10% SDS-PAGE gels, and the proteins were electrotransferred onto nitro-cellulose membranes. Western blot detection of cyclin D1 expression was performed using anti-cyclin D1/2 clone 5D4 monoclonal antibody. anti-PCDGF antibodies block PCDGF-induced cyclin D1 expression (FIG. 5).

EXAMPLE 5

The Effect Of PCDGF Receptor Antibody 6G8 On Phosphorylation Of MAPK $2 \times 10^5$/ml MCF-7 cells were plated in 6 well plates in DME/F12 medium plus 5% FBS overnight. The cell culture medium was replaced with phenol-red free DMEM/F12 supplemented with 5% charcoal-stripped FBS and cultured for 1 day. The cell culture medium was then replaced with serum free, phenol-red free medium for another 1 day. After treatment with PCDGF (200 ng/ml), 6G8 (50 µg/ml) or PCDGF with 6G8 for ten minutes, the cells were lysed with RIPA buffer plus protein inhibitors. 60 µg of whole cell lysates were separated by 10% SDS-PAGE gels, and the proteins were electrotransferred onto nitro-cellulose membranes. Western blot detection of phospho-MAPK expression was performed using anti-phospho-p44/42 MAPK (Thr202/Thr204) E10 monoclonal antibody (FIG. 6). In the control lane, no phosphorylated MAPK was detected. PCDGF stimulated the phosphorylation of MAPK, a key cell signal protein in cells. 6G8 antibody alone has no effect. However, the addition of 6G8 blocks PCDGF-induced phosphorylation of MAPK.

EXAMPLE 6

The Effect of PCDGF Receptor Antibodies on the Proliferation of Human Breast Cancer Cells MCF-7 cells were plated in 24-well plates at $10^5$ cells per well in DME/F12 medium plus 5% FBS. Two days later, the medium was replaced with phenol-red free DMEM/F12 supplemented with 5% charcoal-stripped FBS. After another 24 hours of synchybation, the medium was replaced with serum free, phenol-red free DME/F12 medium. 200 ng/ml PCDGF or 50 µg/ml 6G8, 4H11 or 50 µg/ml non-immune IgG was added into the wells in triplicate. $^3$H-thymidine was added 24 hours later and after 5 hours labeling, cells were lysed and radioactivity was counted by a liquid scintillation counter. Anti-PCDGF receptor antibodies significantly reduced the proliferation of MCF-7 cells as shown in FIG. 8.

What is claimed is:

1. A method of reducing proliferation of a breast cancer cell, comprising:
   contacting the cell with an anti-PCDGF receptor antibody or antigen-binding fragment thereof in an amount effective to reduce proliferation of said breast cancer cell.

2. The method of claim 1, wherein said anti-PCDGF receptor antibody is produced by a hybridoma cell line selected from the group consisting of 6G8 (ATCC Accession Number PTA-5263) and 5A8 hybridoma cell line (ATCC Accession Number PTA-5594) or an antigen-binding fragment thereof.

3. The method of claim 1, wherein said antibody or fragment is chimerized.

4. The method of claim 1, wherein said antibody or fragment is humanized.

5. The method of claim 1, wherein said fragment is selected from Fab, F(ab)$_2$, Fab', F(ab')$_2$, Fd, Fd', Fv and scFv.

6. A method of inhibiting growth of a breast cancer cell, comprising:
   contacting the cancer cell with an anti-PCDGF receptor antibody or antigen-binding fragment thereof in an amount effective to inhibit growth of said breast cancer cell.

7. The method of claim 6, wherein said anti-PCDGF receptor antibody is produced by a hybridoma cell line selected from the group consisting of 6G8 (ATCC Accession Number PTA-5263) and 5A8 hybridoma cell line (ATCC Accession Number PTA-5594) or an antigen-binding fragment thereof.

8. The method of claim 6, wherein said antibody or fragment is chimerized.

9. The method of claim 6, wherein said antibody or fragment is humanized.

10. The method of claim 6, wherein said fragment is selected from Fab, F(ab)$_2$, Fab', F(ab')$_2$, Fd, Fd', Fv and scFv.

11. A method of treating breast cancer in a patient, comprising:
    administering to the patient an anti-PCDGF receptor antibody or an antigen-binding fragment thereof in an amount effective to treat breast cancer in said patient.

12. The method of claim 11, wherein said anti-PCDGF receptor antibody is produced by a hybridoma cell line selected from the group consisting of 6G8 (ATCC Accession Number PTA-5263) and 5A8 hybridoma cell line (ATCC Accession Number PTA-5594) or an antigen-binding fragment thereof.

13. The method of claim 11, wherein said antibody or fragment is chimerized.

14. The method of claim 11, wherein said antibody or fragment is humanized.

15. The method of claim 11, wherein said fragment is selected from Fab, F(ab)$_2$, Fab', F(ab')$_2$, Fd, Fd', Fv and scFv.

16. The method of claim 11, wherein said patient is human.

* * * * *